(12) United States Patent
Shen et al.

(10) Patent No.: US 9,616,617 B2
(45) Date of Patent: Apr. 11, 2017

(54) SCALABLE BIOCHIP AND METHOD FOR MAKING

(71) Applicant: Taiwan Semiconductor Manufacturing Company, Ltd., Hsin-Chu (TW)

(72) Inventors: Wei-Cheng Shen, Tainan (TW); Yi-Shao Liu, Zhubei (TW); Yi-Hsien Chang, Shetou Township (TW); Chun-Ren Cheng, Hsin-Chu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 194 days.

(21) Appl. No.: 13/790,828

(22) Filed: Mar. 8, 2013

(65) Prior Publication Data

US 2014/0256030 A1  Sep. 11, 2014

(51) Int. Cl.
*B01L 3/00* (2006.01)
*B29C 65/72* (2006.01)
*G01N 27/414* (2006.01)

(52) U.S. Cl.
CPC ........ *B29C 65/72* (2013.01); *B01L 3/502707* (2013.01); *B01L 2300/0636* (2013.01); *B01L 2300/0887* (2013.01); *G01N 27/4145* (2013.01)

(58) Field of Classification Search
None
See application file for complete search history.

(56) References Cited

U.S. PATENT DOCUMENTS

| | | | |
|---|---|---|---|
| 5,962,081 A * | 10/1999 | Ohman et al. | 427/534 |
| 2008/0017306 A1* | 1/2008 | Liu et al. | 156/297 |
| 2009/0111168 A1* | 4/2009 | Kim et al. | 435/287.1 |

FOREIGN PATENT DOCUMENTS

CN    1603761 A    4/2005

OTHER PUBLICATIONS

Leichlé, Thierry et al., "Biosensor-compatible encapsulation for pre-functionalized nanofluidic channels using asymmetric plasma treatment," SciVerse ScienceDirect, Sensors and Actuators B, 161, www.elsevier.com/locate/snb, 2012, pp. 805-810.

* cited by examiner

*Primary Examiner* — Rebecca Martinez
(74) *Attorney, Agent, or Firm* — Slater Matsil, LLP

(57) ABSTRACT

The present disclosure provides a biochip and methods of fabricating. The biochip includes a fluidic part and a sensing part bonded together using a polymer. The fluidic part has microfluidic channel pattern on one side and fluidic inlet and fluidic outlet on the other side that are fluidly connected to the microfluidic channel pattern. The fluidic inlet and fluidic outlet are formed by laser drilling after protecting the microfluidic channel pattern with a sacrificial protective layer. The polymer bonding is performed at low temperature without damaging patterned surface chemistry on a sensing surface of the sensing part.

20 Claims, 14 Drawing Sheets

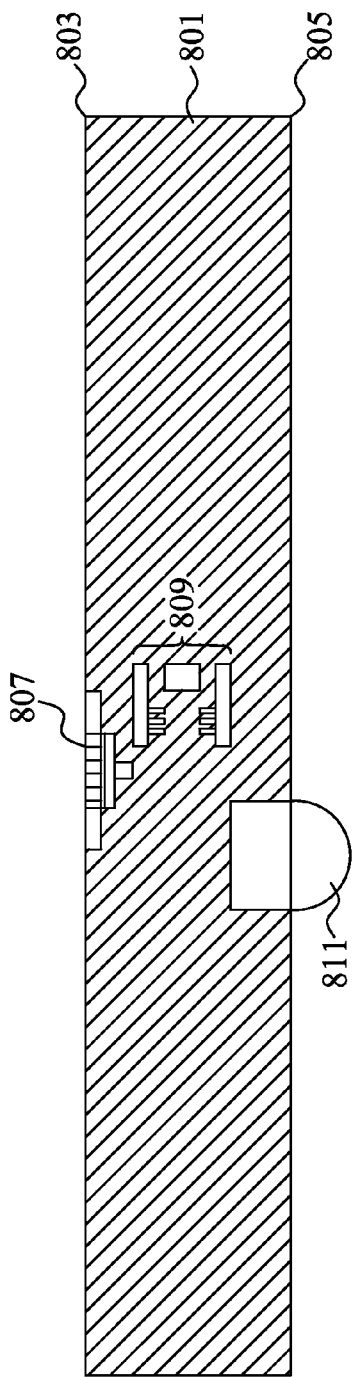
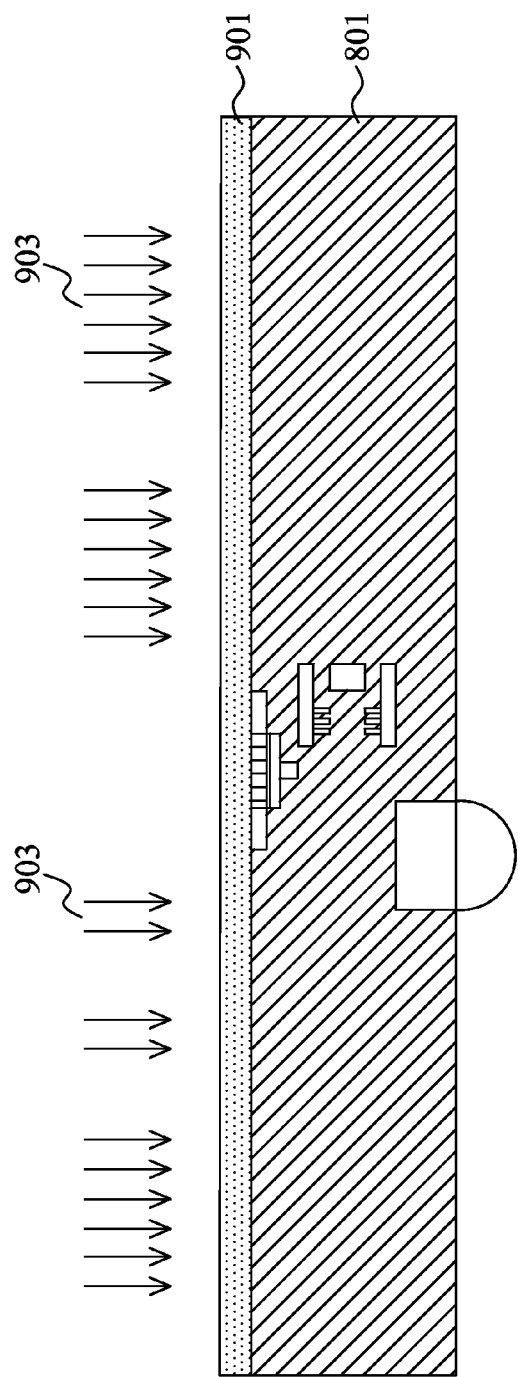

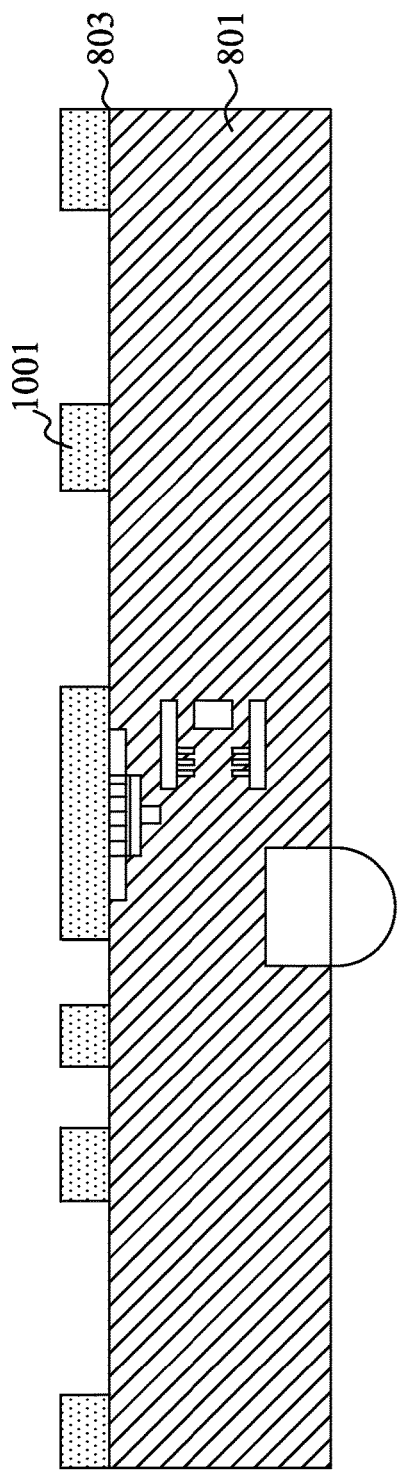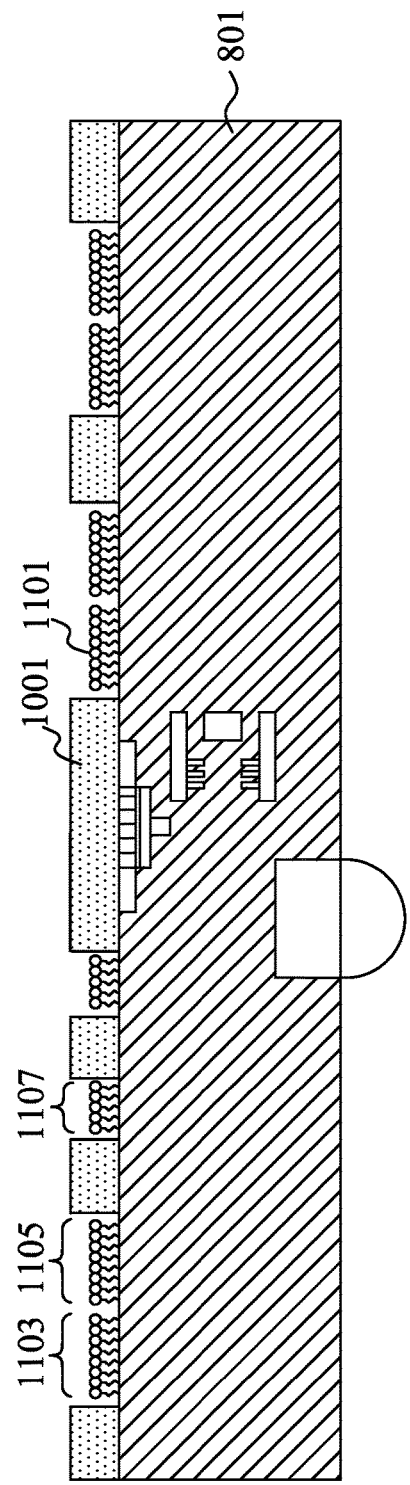

SCALABLE BIOCHIP AND METHOD FOR MAKING

FIELD

This disclosure relates to biosensors and methods for forming bio-chips. Particularly, this disclosure relates to bio-chips having biosensors and fluidic devices and methods for forming them.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and microelectromechanical systems (MEMS).

Biochips are essentially miniaturized laboratories that can perform hundreds or thousands of simultaneous biochemical reactions. Biochips can detect particular biomolecules, measure their properties, process the signal, and may even analyze the data directly. Biochips enable researchers to quickly screen large numbers of biological analytes for a variety of purposes, from disease diagnosis to detection of bioterrorism agents. Advanced biochips use a number of biosensors along with fluidic channels to integrate reaction, sensing and sample management. While biochips are advantageous in many respects, challenges in their fabrication and/or operation arise, for example, due to compatibility issues between the semiconductor fabrication processes, the biological applications, and restrictions and/or limits on the semiconductor fabrication processes.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIGS. 3-4, 5A-5C, 6, 7A-7C, and 8-17 are cross-sectional views of partially fabricated biochip devices constructed according to one or more steps of the method of FIGS. 2A to 2C according to one or more aspects of the present disclosure.

DETAILED DESCRIPTION

Figure 1:
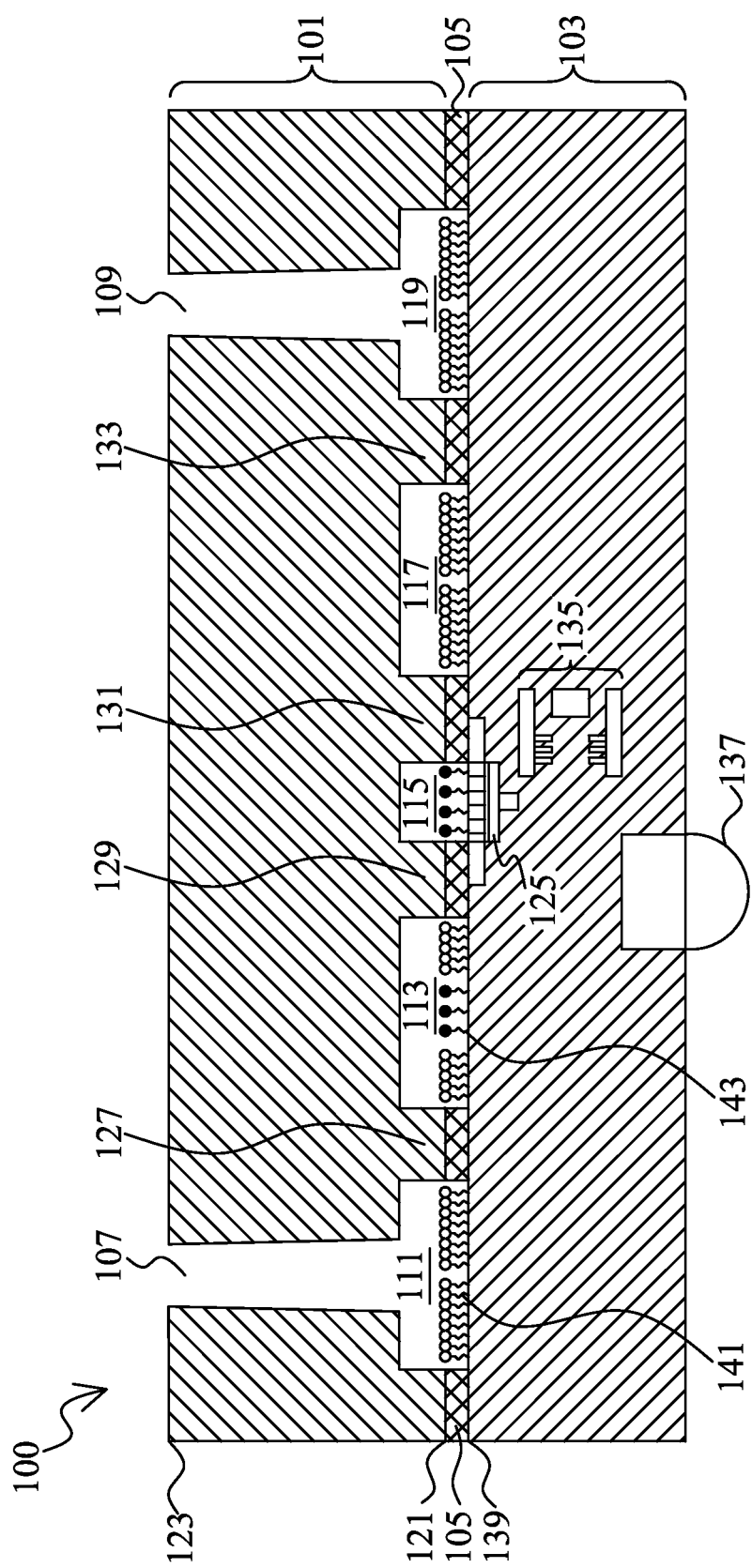
FIG. 1 is a cross-sectional view of a biochip in accordance with various embodiments of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

A simple conventional biochip involves various bioreceptors which react with various biological material of interest in one or more wells. One common approach is to tag a reaction with a fluorescent or phosphorescent bioreceptor that emits a detectible photon. A coordinated approach would encode the sensor to a location on the biochip, so that a positive reaction and photo-detection would be correlated to the location to determine the nature of the reaction, for example, identity of the biological material. The signal may be optical, magnetic, electrical or a mass-sensitive measurement such as surface acoustic wave or microbalance weights. A random approach is to encode the sensor with different fluorescence, phosphorescence, or otherwise detectible and differentiable sensors. A positive detection would be correlated to the type of signal transduced to determine the nature of the reaction. The signal transduced may be photons, for example, a different wavelength light is generated for different biological materials or surface plasmon resonance.

More advanced biochips involve not only biosensors, but also various fluidic channels to deliver biological material to the sensors. The fluidic channels may be a part of a microfluidic system that includes pumps, valves, and various measurement devices such as flow meters, pressure transducers, and temperature sensors. Because a biochip combines electrical processing and fluid processing, fluid handling ability has to successfully integrate within a semiconductor chip environment. A potential use of biochips is as a lab-on-a-chip—where medical professionals can use a small biochip to perform testing in the field, obtain results contemporaneously, and proceed with treatment or further analysis without retreating to a laboratory. Especially for medical professionals working in remote areas where sample preservation may be difficult, lab-on-a-chip devices can save lots of traveling and waiting. These lab-on-a-chip devices are often single-use, or disposable, devices. As such, the manufacturing costs have to be low to be economically viable.

Semiconductor processing often involves baking, curing, and exposing various surfaces to plasma energy and radiation energy. At high temperatures (i.e., above about 60 degrees Celsius) and/or high energies, these processes would damage or destroy bioreceptors, which usually are delicate bio-molecules. For example, the bioreceptors may be antibodies/antigens, enzymes, nucleic acids/DNA, cellular structures/cells, and biomimetic receptors. DNA and enzymes becomes damaged or are destroyed at temperatures above 100 degrees Celsius. Proteins and cells may be damaged or destroyed at temperatures about or above 60 degrees Celsius. Thus, the bio-functionalization of surfaces when bio-molecules are attached, are often performed after all the semiconductor processes are completed. In some designs, the fluidic channels are formed directly on the semiconductor substrate, usually silicon wafer, along with the biosensors. The fluidic channel formation, usually etching, on the silicon directly can damage the biosensors. Dry etching uses much material, time, and energy to etch the channel size in silicon. However, wet etch is harder to control.

According to various embodiments, the biochips are formed by bonding two substrates: a fluidic substrate where the microfluidic channels are formed, and a sensing wafer on which the biosensors and the bioreceptors are attached. The various embodiments of the present disclosure contemplates a process and a biochip that allows bio-functionalization to occur before the bonding of the fluidic substrate and the sensing wafer at about room temperature without damaging the biomolecules with high temperature, high energy semiconductor processes. Further, the fluidic substrate includes microfluidic channels and inlets/outlets. The fluidic substrate is formed separately from the sensing wafer and total cycle time is reduced.

FIG. 1 is a cross-section of a biochip 100 in accordance with various embodiments of the present disclosure. The biochip 100 includes a fluidic substrate 101 and a sensing wafer 103 with a bonding polymer 105 between. The bonding polymer 105 is a biologically compatible material that does not react with the analyte, bioreceptors, or any testing fluid. The bonding polymer may be a photoresist. In one example, the photoresist is polysilesequioxane (PSQ).

The fluidic substrate 101 has a fluidic inlet 107/109 and a fluidic outlet 109/107 through the fluidic substrate 101. The fluidic substrate 101 has a first surface 121 and a second surface 123. The first surface 121 includes microfluidic channel patterns, shown as channels and wells 111, 113, 115, 117, and 119, referred herein collectively as cavities. The various cavities 111, 113, 115, 117, and 119 are connected to each other via various pathways and may be different sizes depending on the design of the biochip. Some of the cavities may match a biosensor, providing a well having a sensing surface. Some of the cavities may be a fluidic reservoir. Some of the cavities may include bioreceptors that would react detectibly with an analyte. The fluidic substrate 101 features between the cavities are island features, for example, island features 127, 129, 131, and 133. According to various embodiments, the island features include a flat portion that is bonded to the bonding polymer 105 and hence through the bonding polymer 105 to the sensing wafer 103.

The sensing wafer 103 includes a patterned sensing surface 139 and one or more biosensors 125. The biosensors may be a biological field-effect transistor (BioFET), an optical sensor (for example, a CMOS sensor), electrochemical biosensors, and mass sensitive sensor (for example, with embedded piezoelectric crystals). The biosensor 125 is connected through an interconnect structure 135 to one or more electrodes 137. The electrodes 137 provide power and input/output of electrical signals to the biochip. The electrodes 137 may be bumps such as a ball grid array, copper pillars, or solder material. In various embodiments, the electrodes 137 allows a reading of the data collected from the sample and may further allow control of the biological analysis. The biochip may be inserted into a module having corresponding electrode pads that further includes input/output devices and a power supply. Although only one biosensor is depicted in FIG. 1, each of the cavities 111, 113, 115, 117, and 119 may have a corresponding biosensor.

In some embodiments, the biosensor is external to the sensing wafer and only a patterned sensing surface 139 is provided. The presence of analyte and/or reaction is detected externally through the one or more transparent substrates 101 or 103. In such embodiments, the biochip 100 may be inserted into a photodetector which would activate the reaction and analyze the extent or identity of the analyte through a positive photodetection at a coordinate on the biochip or a positive photodetection of a particular type of photon.

As shown in FIG. 1, the patterned sensing surface 139 includes two types of bioreceptors 141 and 143. Each cavity may include only one type of bioreceptor, such as cavities 111, 115, 117, and 119. A cavity may also include more than one type of bioreceptors, such as cavity 113 having both bioreceptors types 141 and 143. The bioreceptors may have different densities as shown and may have an internal pattern in a cavity. For example, cavities 111 and 119 both include bioreceptors 141 arranged in two groups in a cross section. The various embodiments of the present disclosure include having multiple types of patterned bioreceptors on the sensing surface 139. In some embodiments, random bioreceptors may be included in addition to patterned bioreceptors.

Figure 2A:
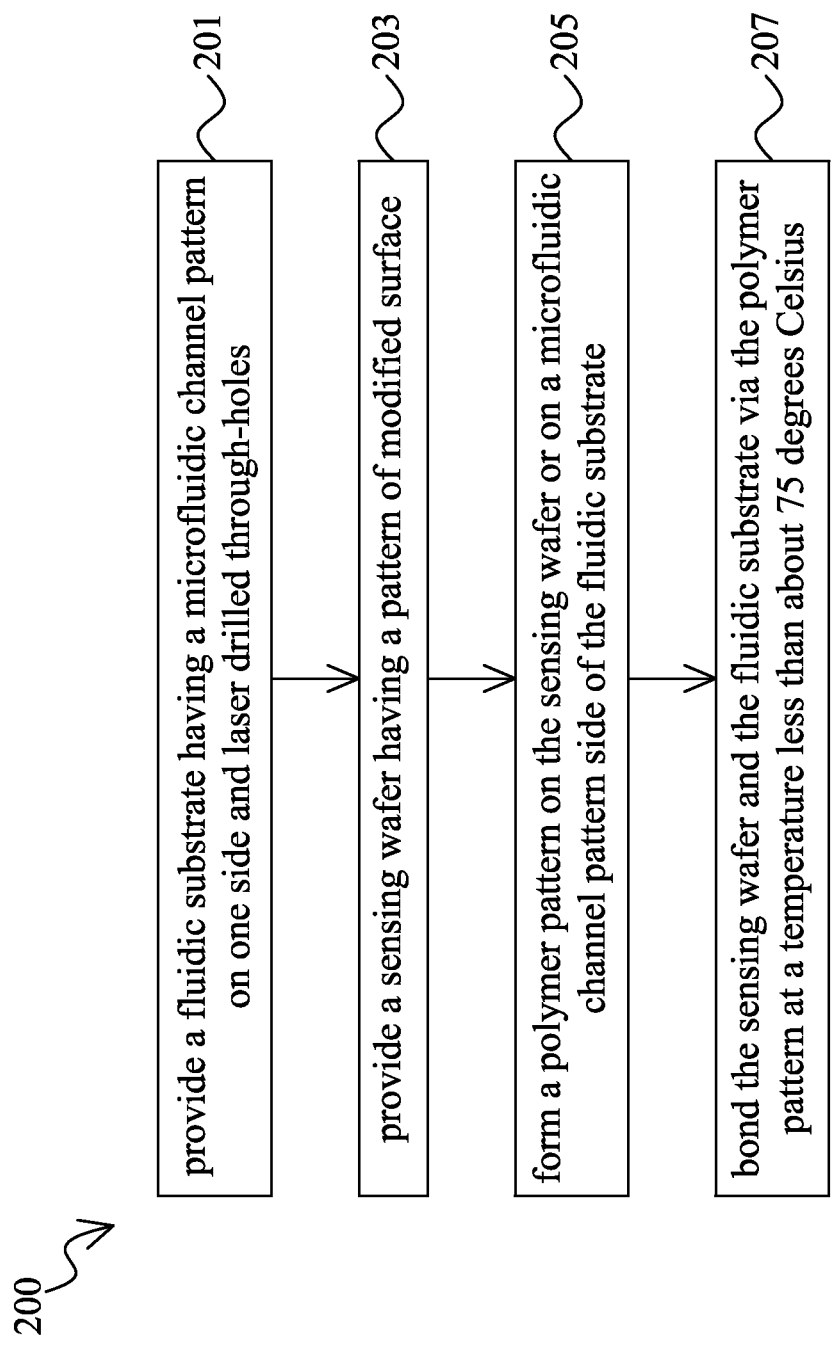
FIGS. 2A-2C are flow charts of various embodiments of methods of fabricating a biochip device according to one or more aspects of the present disclosure.
Figure 2B:
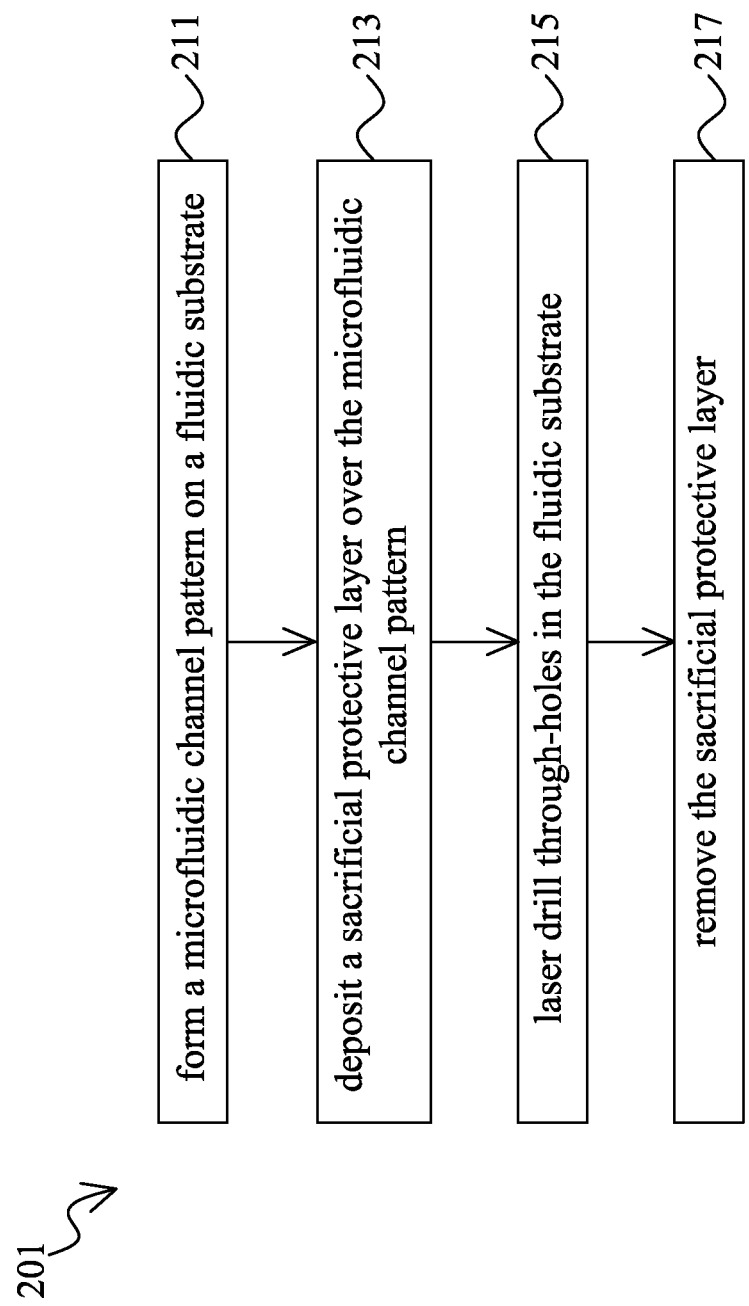
Figure 2C:
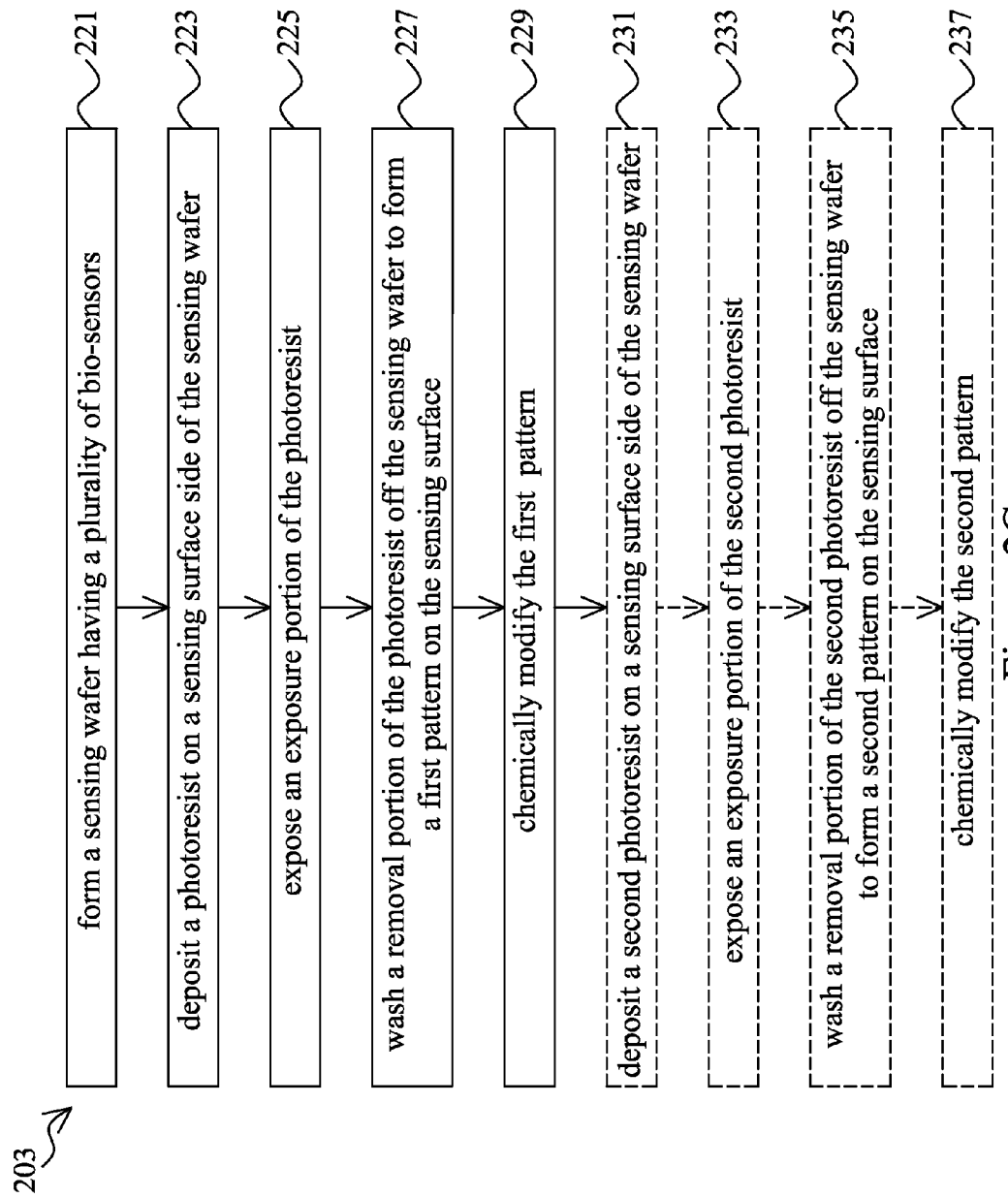

FIGS. 2A and 2C are flow charts of various embodiments of methods of fabricating a biochip device according to one or more aspects of the present disclosure. FIGS. 3-4, 5A-5C, 6, 7A-7C, and 8-17 are cross-sectional views of partially fabricated biochip devices constructed according to one or more steps of the method of FIGS. 2A to 2C. In operation 201 of FIG. 2A, a fluidic substrate having a microfluidic channel pattern on one side and laser drilled through holes are provided. In some embodiments, the fluidic substrate is formed by an entity other than the entity forming the sensing wafer. In other embodiments, the same entity forms both the fluidic substrate and the sensing wafer.

Figure 3:
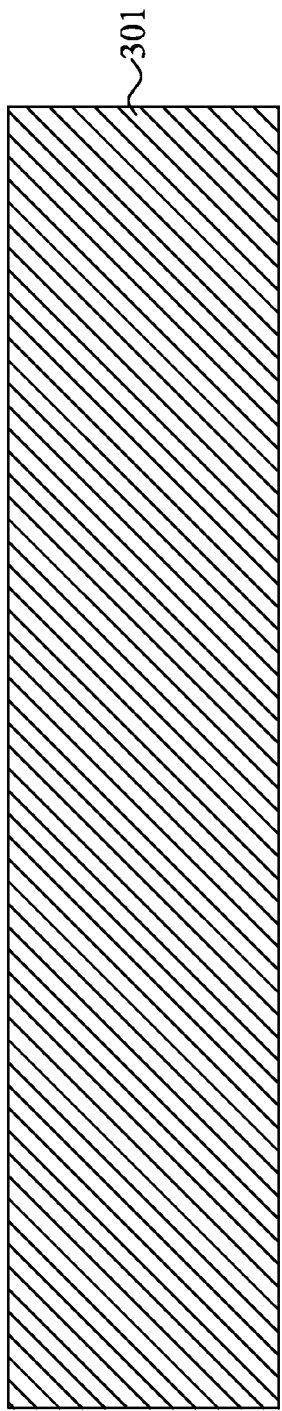
Figure 4:
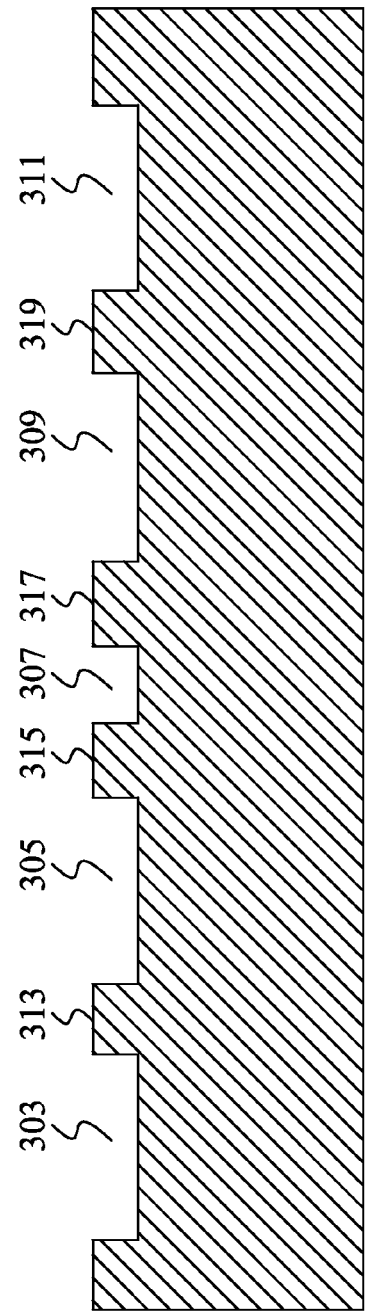

FIG. 2B shows further details of the operation 201. In operation 211, a microfluidic channel pattern is formed on a fluidic substrate. FIG. 3 shows a fluidic substrate 301. The fluidic substrate 301 may be quartz, glass, silicon, sapphire, or other suitable substrate material that does not react with the analyte or solution. According to some embodiments, the fluidic substrate may be at least ten microns thick or about 11 microns thick. The fluidic substrate 301 may be transparent or opaque, depending on whether the biochip is designed for external photo-detection or inspection.

A microfluidic channel pattern is formed first by patterning a photoresist (not shown) over the substrate 301 with a channel pattern. After developing the photoresist and removing portions of the photoresist, the remaining photoresist is used as a pattern to etch the microfluidic channel pattern of FIG. 4. The microfluidic channels 303, 305, 307, 309, and 311 are etched into the fluidic substrate 301 by wet etch or dry etch. In some embodiments, a dry etch is used to form channels and wells at about 100 nm. The various channels and wells connect to each other in a network of microfluidic channels. Other features including pumps, valves, sensors, and other micro-electro-mechanical system (MEMS) devices may be formed or embedded in the fluidic substrate 301. The field regions between the channels and wells are island features, for example, features 313, 315, 317, and 319. The fluidic substrate 301 will be eventually bonded to a sensing wafer at these island features with a bonding polymer. To avoid leakage between adjacent channels and wells, the bonding polymer hermetically seals the channels and wells from each other. A better seal is achieved by ensuring a good match between the surface of the island features and the sensing wafer. Thus, various processes are designed to ensure at least a portion of the top of the island features remain flat and available for good adhesion. For example, processes that result in underetching of the substrate 301 under the photoresist is avoided or minimized.

Referring back to FIG. 2B, in operation 213 a sacrificial protective layer is deposited over the microfluidic channel pattern. The sacrificial protective layer conformally cover the microfluidic channel pattern. In some embodiments, the sacrificial protective layer is a thermally deposited silicon oxide (thermal oxide). The thermal oxide may be deposited by exposing the fluidic substrate 301 to oxygen (dry oxidation) or steam (wet oxidation) at a high temperature, typically above 500 degrees Celsius or between about 800 degrees Celsius and 1200 degrees Celsius. The thermal oxide is sometimes referred to as a high temperature oxide. The thermal oxide is grown by consuming a portion of the fluidic substrate 301. The thermal oxide thickness may be at least 5 nm and may be as much as 100 nm.

In other embodiments, the sacrificial protective layer is deposited without consuming a portion of the fluidic substrate 301. The sacrificial protective layer may be a silicon oxide deposited using various conventional chemical vapor deposition (CVD) techniques, such as plasma enhanced (PE) CVD, low-pressure (LP) CVD, high density plasma (HDP) CVD, and atomic layer deposition (ALD). The CVD oxide thickness may be at least 5 nm and may be as much as 100 nm.

In addition to silicon oxide, other conformally deposited material may be used, for example, a metal oxide. Because the sacrificial protective layer is to be removed, any conformally deposited material that can protect the surface of the microfluidic channel pattern during laser drilling and that can be removed completely may be used. Further, the sacrificial protective layer material may be bio-compatible.

Figure 5A:
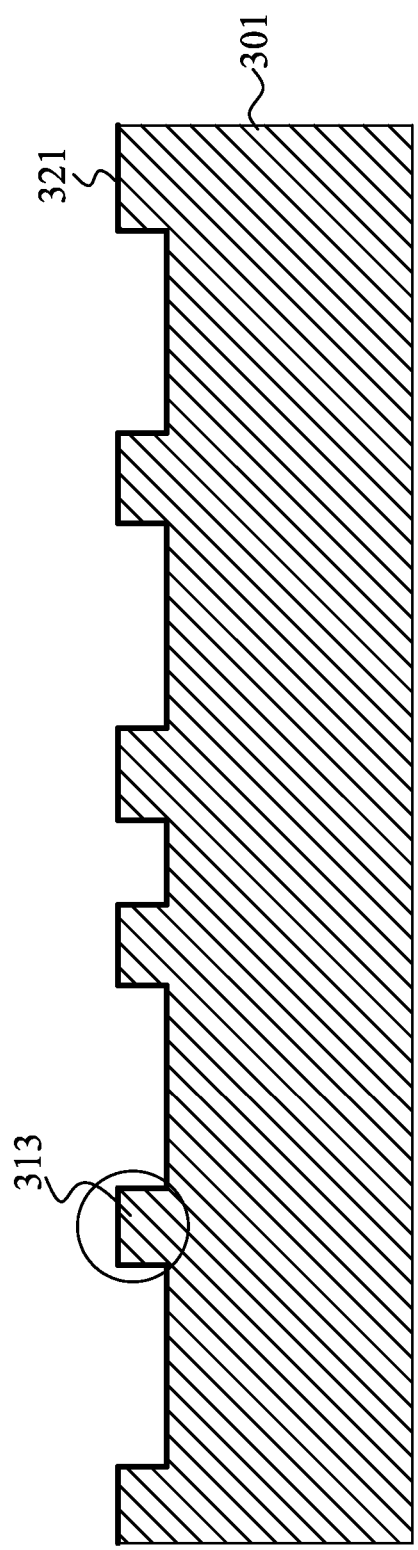
Figure 5B:
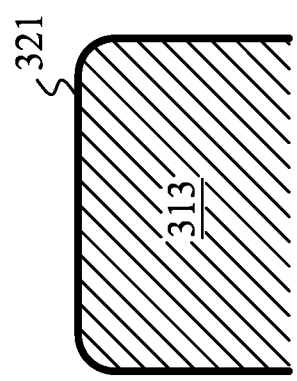
Figure 5C:
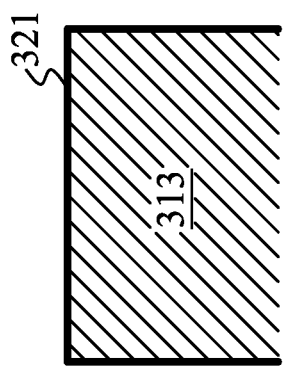

FIG. 5A shows a fluidic substrate 301 with a sacrificial protective layer 321 over the microfluidic channel pattern including island feature 313. FIGS. 5B and 5C show details of the island feature 313. FIG. 5B is an embodiment of a thermal oxide sacrificial protective layer 321. Because the thermal oxidation process consumes the fluidic substrate, corners of the island feature 313 is slightly rounded because the corners are attacked form both sides. However, a substantial portion of a top of the island feature 313 remains flat or substantially flat. For example, the radius of curvature at the island edges may be around 20 to 25% of the thermal oxide thickness. In another example, for an island feature having a width about 100 nm, greater than about 75% of the top surface remains flat. FIG. 5C is an embodiment of a CVD oxide sacrificial protective layer 321 over the island feature 313. The corners of the island feature 313 of FIG. 5C are less rounded than that of FIG. 5. Because the CVD process does not consume the underlying substrate and does deposits material over it, the underlying shape is preserved and a maximum amount of flat area may be used to bond the fluidic substrate with the sensing wafer.

Figure 6:
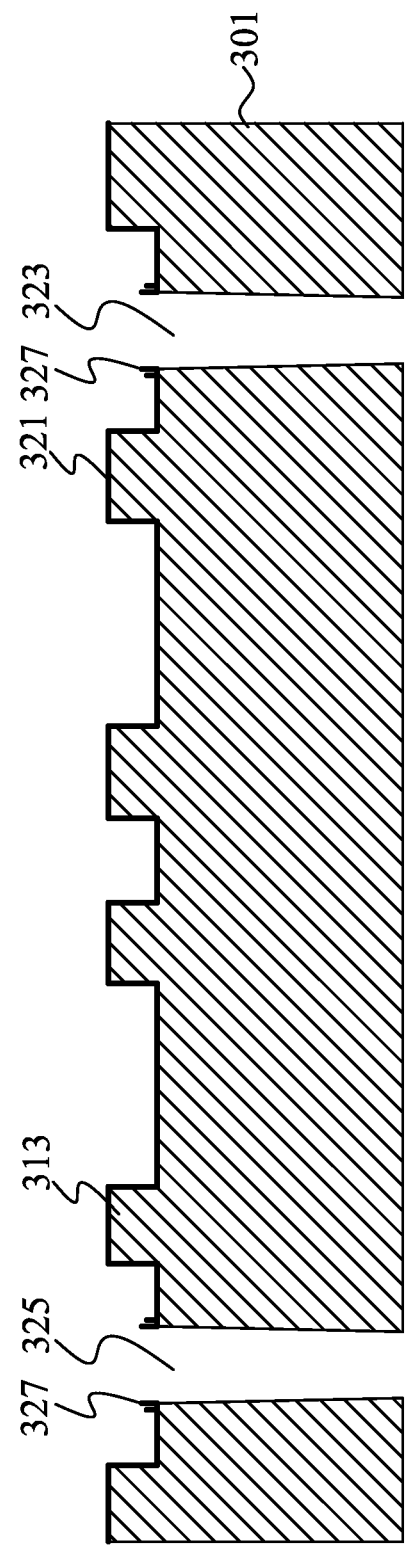

Referring back to FIG. 2B, in operation 215, through-holes are laser drilled in the fluidic substrate. FIG. 6 is a cross-sectional view of a fluidic substrate 301 with a sacrificial protective layer 321 over the microfluidic channel pattern and laser drilled through holes 323 and 325. Laser drilling of cylindrical holes generally occurs through melting and vaporization (also referred to as "ablation") of the substrate material through absorption of energy from a focused laser beam. The laser drilling process results in a melt expulsion from the substrate. Melt expulsion arises as a result of the rapid build-up of gas pressure (recoil force) within a cavity created by evaporation. For melt expulsion to occur, a molten layer must form and the pressure gradients acting on the surface due to vaporization must be sufficiently large to overcome surface tension forces and expel the molten material from the hole. In a fluidic substrate, the melt expulsion results in fine liquid particles being expelled from the hole at a high velocity. Some of the fine liquid particles condense and adhere on the substrate.

FIG. 6 shows these small fragments 327, condensed melt expulsion particles, next to edges of the laser drilled holes 323 and 325. If the fluidic substrate 301 is exposed, these small fragments 327 sinter onto the fluidic substrate 301. Thus attached, these small fragments 327 cannot be removed cleanly, without affecting surrounding features. For example, one way to remove these small fragments is by chemical mechanical polishing (CMP) of the microfluidic channel pattern side of the fluidic substrate 301. The slurry used in CMP and the polishing motion not only removes the small fragments, but also rounds out the island features 313 to make the island features into a mound shape that does not have a substantial portion on the top that is flat. A mound shaped island feature does not bond well to a sensing wafer and may allow leakage across different fluidic channels and wells.

Depending on the direction of the laser energy, the laser drilled through holes 323 and 325 can have the inverse trapezoidal shape in a cross section as shown in FIG. 6 or a trapezoidal shape. In order to assure alignment, the laser drilling is performed from the microfluidic channel pattern side of the substrate 301.

Figure 7A:
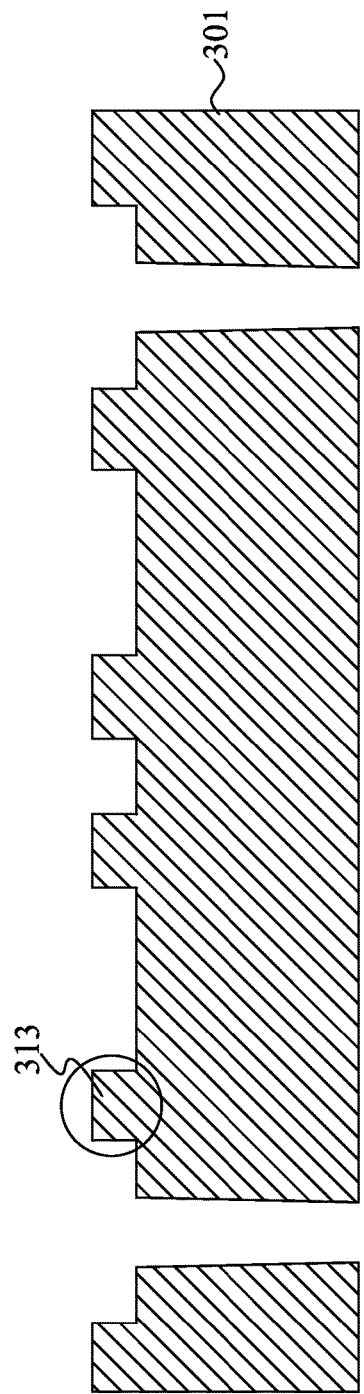
Figure 7B:
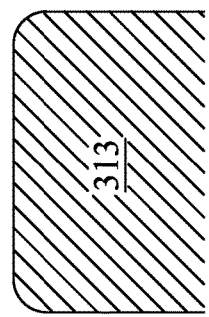
Figure 7C:
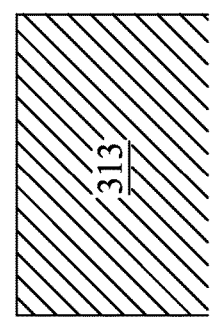

Referring back to FIG. 2B, in operation 217, the sacrificial protective layer is removed. Removal of the sacrificial protective layer also removes the small fragments because with the sacrificial protective layer, the small fragments do not sinter onto the substrate. The sacrificial protective layer may be removed by conventional wet etch or dry etch processes. FIG. 7A is a cross sectional diagram of a fluidic substrate 301 after the sacrificial protective layer are removed. FIGS. 7B and 7C are close-ups of the cross sectional diagram showing the island feature 313. In FIG. 7B, the island feature 313 has a rounded corner corresponding to having thermal oxide sacrificial protective layer removed. In FIG. 7C, the island feature 313 has a sharp right corner corresponding to having CVD oxide sacrificial protective layer removed. Because the sacrificial protective layer is very thin, the removal etch process is tuned to minimize damage to underlying substrate. After the operation 217, the process returns to method 200 of FIG. 2A.

In operation 203, a sensing wafer having a pattern of modified surface is provided. FIG. 2C shows further details of the operation 203. In operation 221, a sensing wafer having bio-sensors is formed. As discussed, a variety of bio-sensors may be formed in or on a sensing wafer. One example is a BioFET as shown in FIG. 8, formed in a sensing wafer 801 having a sensing surface side 803 and a back side 805. The sensing wafer 801 includes a number of BioFET 807 on the sensing surface side 803. Connected to the BioFETs 807 is the interconnect structure 809, which is also connected to electrodes 811 on the back side 805 of the sensing wafer 801. The BioFETs are formed directly on the sensing wafer using conventional CMOS processes. Other biosensors on the sensing wafer may include electrodes, surface plasmon resonance sensor, potentiometric biosensor, and other biosensors that are compatible with conventional CMOS processes. Additional devices may also be formed directly on the sensing wafer using conventional CMOS processes, for example, various MEMS devices may include resonistors, actuators, valves, accelerometers, pressure sensor, heater, cooler, among others. While FIG. 8 shows BioFET, other biosensors are envisioned and included in the various embodiments of the present disclosure.

Referring back to FIG. 2C, in operation 223 a photoresist is deposited on a sensing surface side of the sensing wafer. FIG. 9 shows the sensing wafer 801 having a photoresist 901 deposited on the sensing surface side 803. The deposition process may include a cure or soft bake to solidify the photoresist. The photoresist 901 is a bio-compatible material. In operation 225, an exposure portion of the photoresist is exposed to a light radiation 903 as shown in FIG. 9. The exposure portion is defined by a photomask through which the light radiation 903 travels. Some light is blocked by the photomask. In operation 227, a removal portion of the photoresist is washed off the sensing wafer to form a first pattern on the sensing surface. The removal portion may be the same as the exposure portion, in cases of positive photoresist where the exposure portion becomes soluble to a photoresist developer. The removal portion may also be a negative of the exposure portion, in cases of negative photoresist where the non-exposed portion is the portion that is soluble to a photoresist developer. In operation 227, the photoresist developer is used to wash off the removal portion of the photoresist and leaving the first pattern behind on the sensing surface. FIG. 10 is a cross sectional diagram showing the sensing wafer 801 after operation 227. Portions of exposed sensing wafer surface 803 and portions covered by the patterned photoresist 1001 form the first pattern.

Referring back to FIG. 2C, in operation 229, the first pattern is chemically modified. In the embodiments of FIG. 11, the chemical modification is performed on the exposed sensing surface between the photoresist patterns. The chemical modification includes one or more of a surface treatment to change properties or attachment of bioreceptors. In some embodiments, the surface treatment renders the sensing surface hydrophilic or hydrophobic. In some embodiments, the surface treatment involves functionalizing the surface with polylysine, aminosilane, epoxysilane or nitrocellulose. In some cases, three dimensional lattice material is applied to chemically or physically entrap biological material. Chemical entrapment involves keeping the biological material by a strong bond. Physical entrapment involves keeping the biological material by not allowing passage through the pores of a gel matrix. Physical entrapment examples include hydrogel and xerogel. One example is sol-gel, which is a glassy silica generated by polymerization of silicate monomers (added as tetra alkyl orthosilicates, such as TMOS or TEOS) in the presence of the biological elements (along with other stabilizing polymers, such as PEG). Another example is acrylate hydrogel, which polymerize upon radical initiation. The chemical surface modification may also include attachment of bioreceptors on the sensing surface. The bioreceptors may be added or coated onto a functionalized surface or may be fixed layer by layer depositions to form the bioreceptors.

The surface functionalization and bioreceptor attachment may be formed in one operation or separately. In some embodiments, the chemical modification operation 229 involves multiple operations. In other embodiments, the chemical modification operation involves only one operation. In some examples, the first pattern is coated first with a functionalizing chemical that forms a bond with a bioreceptors. The functionalizing chemical attaches to the exposed sensing surface but does not attach to the photoresist. The sensing surface is subsequently sprayed, deposited, or otherwise exposed to a dose of bioreceptors, which readily bonds to the functionalizing chemical on the sensing surface. The sensing surface may include other layers of materials deposited as a part of forming the sensing wafer. For example, the sensing surface may include a metal oxide.

According the various embodiments, one or more chemicals, including optionally bioreceptors, may be printed onto the first pattern via a printer head. The printer head releases a small amount of the ink chemical at precise locations. More than one type of ink chemicals may be used for different locations. The combinations of different ink chemicals at the same location may be used to create yet a different bioreceptors. For example, a printer head capable of printing three ink chemicals (A, B, C) may be tuned to generate seven or more bioreceptors (A, B, C, AB, BC, AC, ABC, etc.), depending on the chemicals used. Increasing the number of ink chemicals can exponentially increase the number of different bioreceptors that can be printed. Using the printing technique, the size of the pixel and the bioreceptors or functionalizing chemical concentration can be finely controlled. However, the shrinkage of printer head size, in other words, the pixel size, is limited. Sizes much smaller than one micron is difficult to achieve using current techniques.

Combining the use of printing and the photolithography techniques allow further shrinkage of the sensing surface area. Because photolithography techniques can define an area smaller than a pixel, it can be used to reduce the sensing surface area. For example, a portion of the pixel may be covered by the photoresist, which may be subsequently removed—resulting in a smaller sensing surface area than previously possible using printing alone.

In some other embodiments, the functionalizing and bioreceptors attaching occurs on the photoresist pattern instead of the exposing sensing surface. In certain embodiments, the photoresist polymer may itself be a kind of functionalization by providing a polymer surface that may be susceptible to certain bioreceptors bonding.

FIG. 11 is a cross-sectional diagram of a sensing wafer 801 having a photoresist pattern with surface chemistry 1101 between the photoresists 1001. The surface chemistry 1101 may be deposited onto the wafer by spraying, coating, condensing, or printing. According to various embodiments, the surface chemistry 1101 has a uniform density across the sensing wafer 801. If a printing method is used for depositing, the surface chemistry 1101 may be grouped into pixels, for example, as pixels 1103 and 1105 of FIG. 11. Each pixel is roughly the same size. Smaller pixels may be formed by restricting the size of the available surface, for example, pixel 1107. Larger pixels may be formed by merging adjacent pixels. While, the embodiments of FIG. 11 include only one type of surface chemistry 1101, a printing method can deposit multiple types of surface chemistry 1101 as discussed.

Referring back to FIG. 2C, optional operations 231 to 237 are repeats of operations 223 to 229, with a different pattern and different surface chemistry. Depending on the type of biochip, these operations may be repeated multiple times to form a sensing wafer having a number of different bioreceptors and/or properties. In subsequent operations, care is taken to not damage the bioreceptors and/or the surface chemistry deposited in operation 229. In some embodiments, additional steps to protect the surface chemistry from the photolithographic operation may be performed. For example, a protective layer may be used over the surface chemistry 1101.

Figure 12:
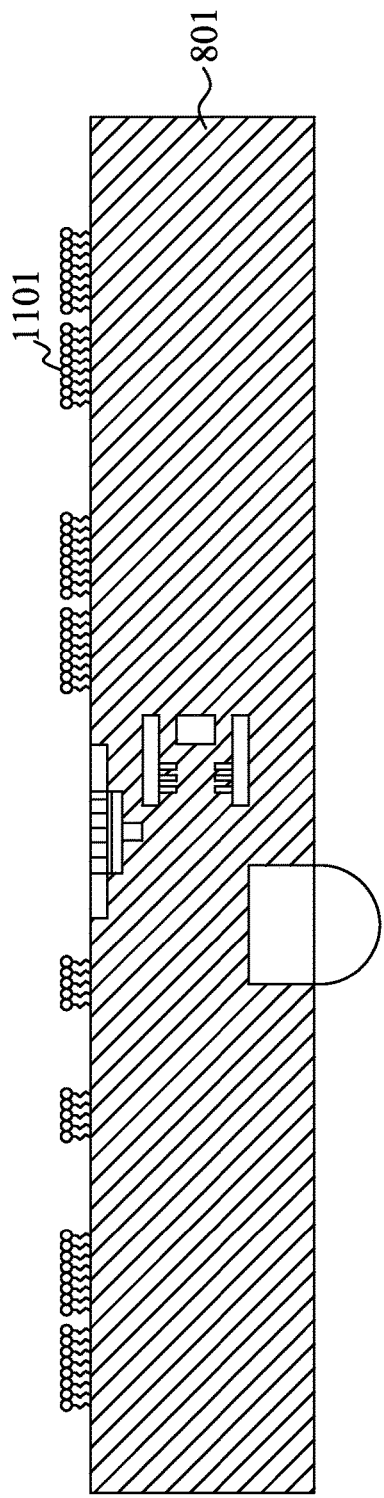
Figure 13:
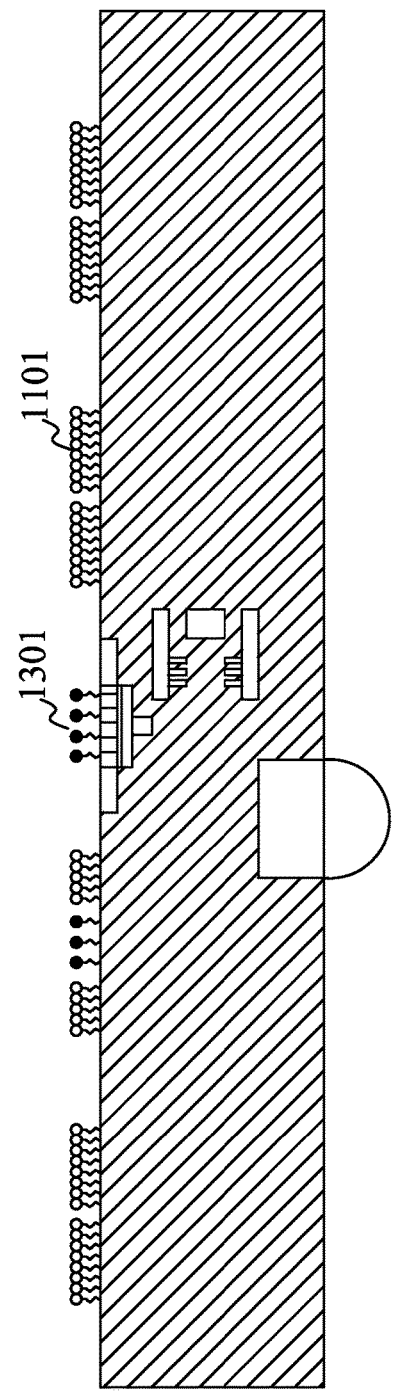

In some embodiments, a second pattern on the sensing wafer is formed using a different method from the first pattern. FIGS. 12 and 13 show cross-sectional diagrams of a sensing wafer where a second pattern is deposited using a printing method directly over a first surface chemistry without a photo pattern. FIG. 12 shows a sensing wafer 801 having surface chemistry 1101 thereon, but the photoresist forming the first pattern has been removed and the sensing wafer surface under the photoresist pattern is exposed. As shown in FIG. 13, a second surface chemistry 1301 is then deposited using a printing technique. Because the printer head does not necessarily need to make direct contact with the surface, a second surface chemistry 1301 may be deposited without affecting the first surface chemistry 1101. As shown, the second surface chemistry 1301 has a different density from the first surface chemistry 1101.

In some embodiments, the photoresist from operation 227 remains a part of the final biochip and thus is not removed. The second surface chemistry 1103 may be deposited on the photoresist on a portion not used for bonding.

Figure 14:
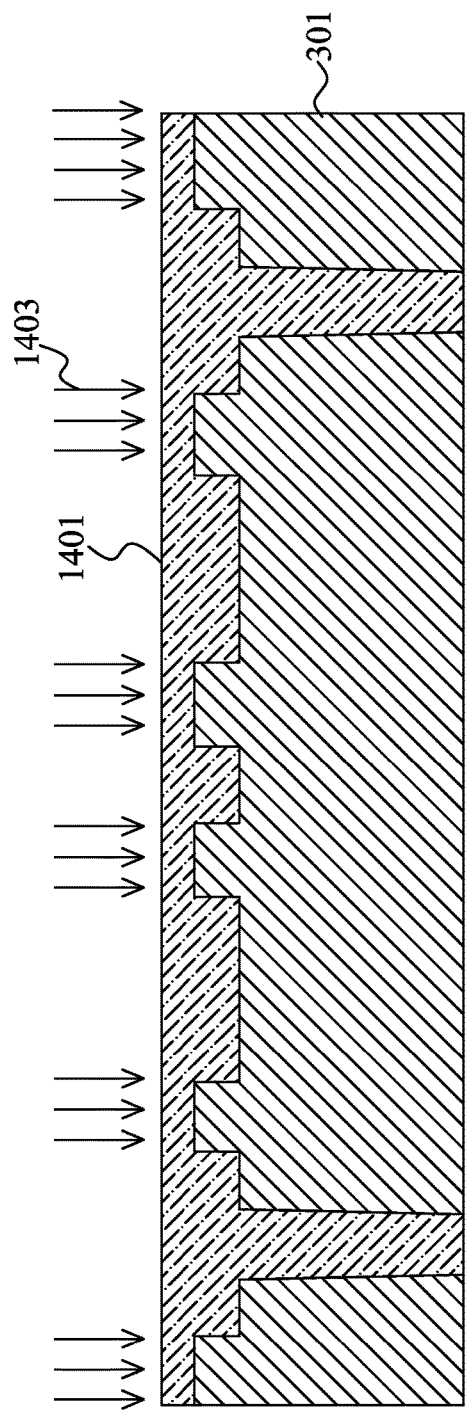
Figure 15:
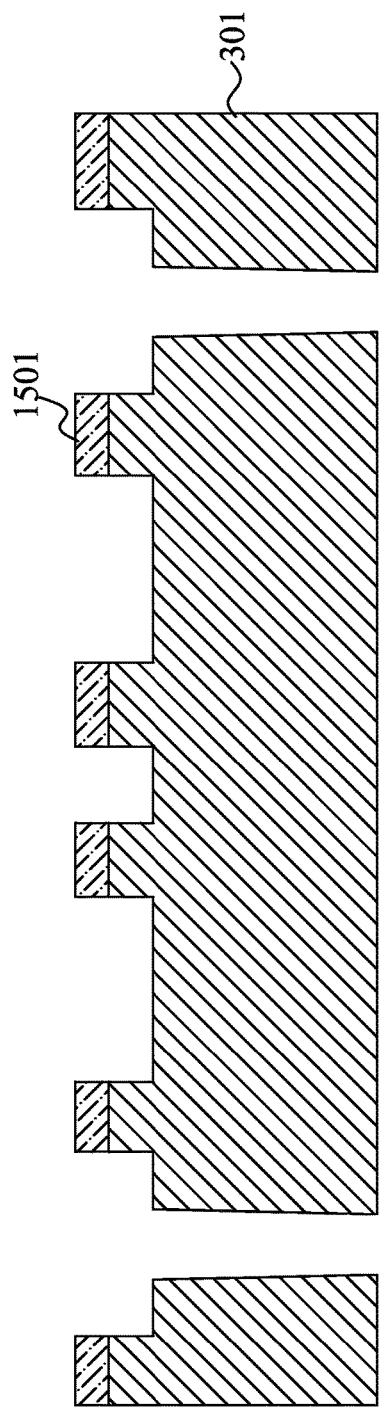

Referring back to FIG. 2A, in operation 205 a polymer pattern is formed on the sensing wafer or a microfluidic channel pattern side of the fluidic substrate. This polymer pattern is used to bond the sensing wafer and the fluidic substrate. According to various embodiments, the polymer is a photoresist. In some embodiments, the polymer is a negative photoresist. The polymer may be polysilesequioxane (PSQ). FIG. 14 is a cross-sectional diagram of a fluidic substrate 301 during the process of forming a polymer pattern. A polymer material 1401 is deposited on the fluidic substrate 301. In this example, the polymer 1401 is a negative photoresist. A light pattern 1403 irradiates the polymer 1401 and changes the chemistry of the photoresist where it is irradiated. The unexposed portion is soluble to a photoresist developer and is washed away during the developing process. What remains is shown in FIG. 15. The polymer portions 1501 define the bonding area to a sensing wafer.

Figure 16:
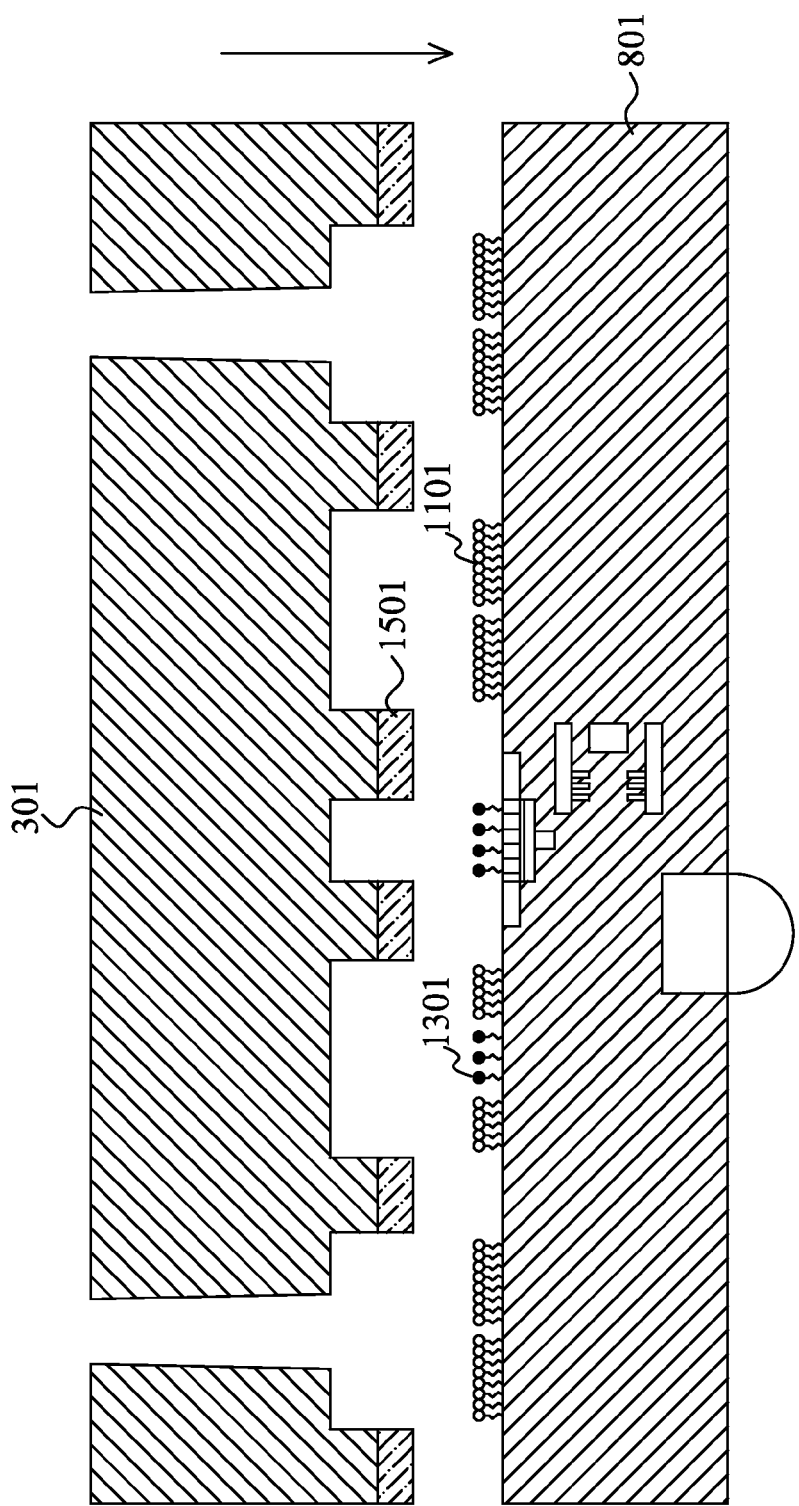

Referring back to FIG. 2A, in operation 207, the sensing wafer and the fluidic substrate is bonded via the polymer pattern at a temperature less than about 100 degrees Celsius or less than about 60 degrees Celsius. According to various embodiments, the polymer surface is treated with a plasma to increase its adhesiveness. The plasma breaks bonds on the polymer surface and creates dangling bonds which readily adhere to a silicon oxide, a thin layer of which is always present on a silicon wafer exposed to ambient conditions. Then the fluidic substrate is flipped over and aligned with the sensing wafer. FIG. 16 shows cross-sectional diagram of a fluidic substrate 301 and a sensing wafer 801 with polymer pattern 1501 and two surface chemistries 1101 and 1301. After alignment, the fluidic substrate and the sensing wafer are placed together. In some embodiments, pressure is applied to ensure even bonding. In other embodiments, one or more of the fluidic substrate and the sensing wafer is heated. However, because the surface chemistries 1101 and 1301 may be sensitive to excessive heat, the sensing wafer 801 temperature may be less than about 60 degrees Celsius, or about room temperature.

Figure 17:
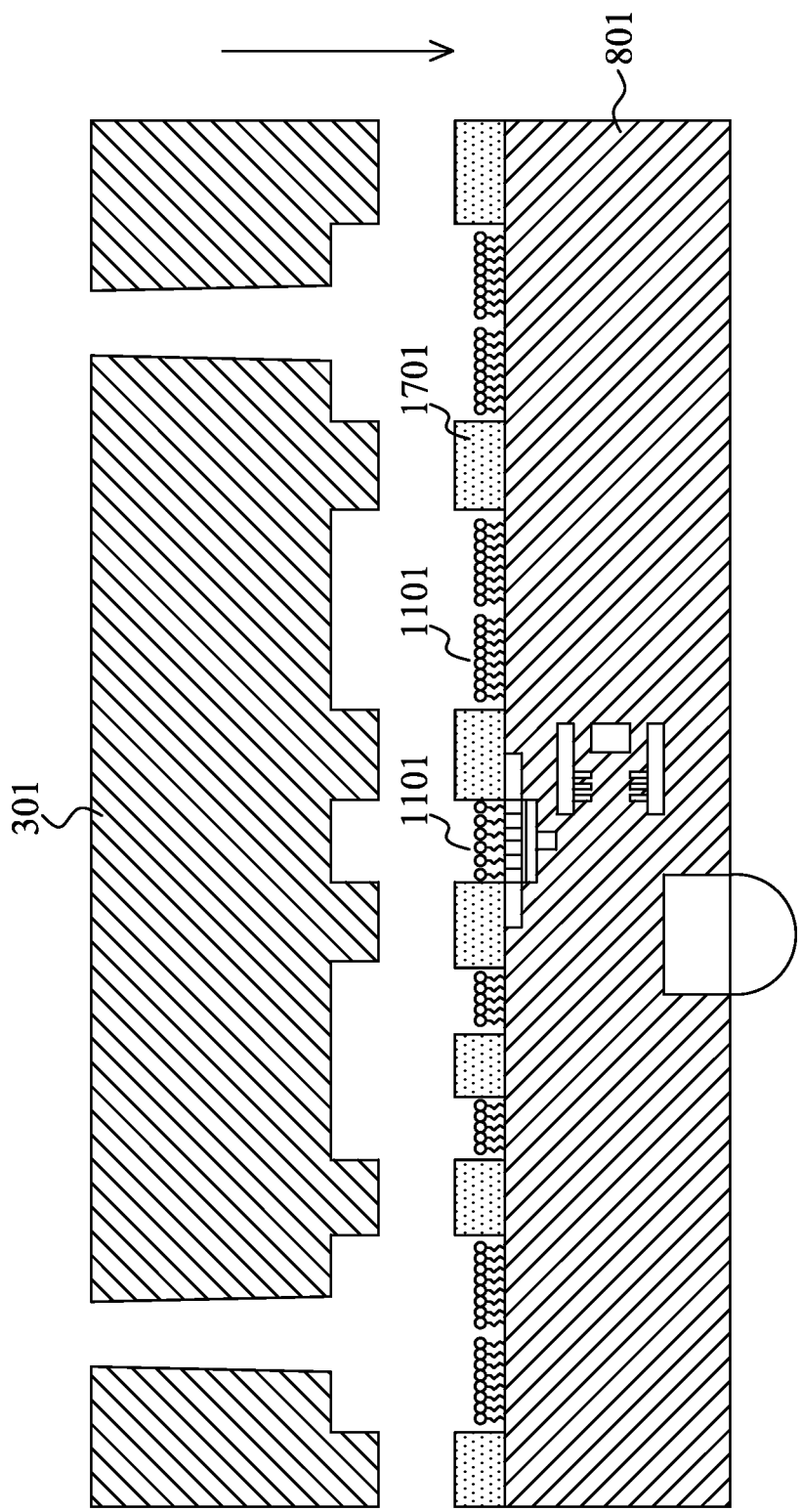

FIG. 17 is an alternative cross-sectional diagram for embodiments where the polymer pattern for bonding is applied to the sensing wafer 801 instead. In certain embodiments, polymer pattern 1701 may be the photoresist pattern 1001 of FIGS. 10 and 11. The photoresist pattern 1001 is treated to increase its adhesiveness for bonding to the fluidic substrate 301. Of course, the treatment is selected to not damage the surface chemistry 1101.

After the fluidic substrate and the sensing wafer are bonded, the integrated workpiece is then diced to form individual biochips. The various embodiments described herein allows one entity, for example, a semiconductor foundry, to manufacturer a biochip without involving a second entity such as a package house.

One aspect of the present disclosure pertains to a method of manufacturing a biochip that includes forming a microfluidic channel pattern on a fluidic substrate, depositing a sacrificial protective layer over the microfluidic channel pattern, laser drilling through-holes in the fluidic substrate, removing the sacrificial protective layer, providing a sensing wafer having a pattern of modified surface, forming a polymer pattern on the sensing wafer or on a microfluidic channel pattern side of the fluidic substrate, and bonding the sensing wafer and the fluidic substrate via the polymer pattern at a temperature less than about 100 degrees Celsius.

Another aspect of the present disclosure pertains to a method of manufacturing a biochip. The method includes providing a fluidic substrate having a microfluidic channel pattern on one side, laser drill through-holes, and no post-laser sintering by-products on the microfluidic pattern; forming a sensing wafer having a plurality of bio-sensors; depositing a photoresist on a sensing surface side of the sensing wafer; exposing an exposure portion of the photoresist; washing a removal portion of the photoresist off the sensing wafer to form a first pattern on the sensing surface; chemically modifying the first pattern; forming a polymer pattern on the sensing wafer or on a microfluidic channel pattern side of the fluidic substrate; and bonding the sensing wafer and the fluidic substrate via the polymer pattern.

In yet another aspect, the present disclosure pertains to a biochip having a fluidic substrate, a sensing device, and a bonding polymer between them. The fluidic substrate includes microfluidic channel pattern on a first side and fluidic inlet and fluidic outlet on a second side. The fluidic inlet and fluidic outlet fluidly are connected to the microfluidic channel pattern. The microfluidic channel pattern includes island features having a flat portion. The sensing device has a plurality of bio-sensors under a sensing surface on a first side having with a first pattern having a first chemistry. The polymer hermetically bonds the first side of the fluidic substrate and the sensing surface side of the sensing device.

In describing one or more of these embodiments, the present disclosure may offer several advantages over prior art devices. In the discussion of the advantages or benefits that follows it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:

1. A method of manufacturing a biochip, comprising:
   forming a microfluidic channel pattern on a fluidic substrate;
   depositing a sacrificial protective layer over the microfluidic channel pattern;
   laser drilling through-holes in the fluidic substrate;
   removing the sacrificial protective layer;
   providing a sensing wafer having a pattern of modified surface;
   forming a polymer pattern on the sensing wafer or on a microfluidic channel pattern side of the fluidic substrate; and
   bonding the sensing wafer and the fluidic substrate via the polymer pattern, after forming the microfluidic channel pattern, at a temperature less than about 100 degrees Celsius, the bonding being done in a manner that the microfluidic channel pattern on the fluidic substrate extends away from the through-holes of the fluidic substrate and along an interface of the fluidic substrate and the sensing wafer.

2. The method of claim 1, wherein the depositing a sacrificial protective layer comprises thermally growing a silicon oxide.

3. The method of claim 1, wherein the temperature is less than about 60 degrees Celsius.

4. The method of claim 1, wherein the removing the sacrificial protective layer comprises wet cleaning.

5. The method of claim 1, wherein the pattern of modified surface includes patterns of bio-functionalization.

6. The method of claim 1, wherein the polymer is a photoresist.

7. The method of claim 1, wherein the bonding the sensing wafer and the fluidic substrate comprises treating a surface of the polymer with plasma and alignably contacting the sensing wafer and the fluidic substrate.

8. The method of claim 1, further comprising dicing the bonded sensing wafer and fluidic substrate into a plurality of biochips wherein the through-holes comprise a fluidic inlet and a fluidic outlet.

9. A method of manufacturing a biochip, comprising:
providing a fluidic substrate having a microfluidic channel pattern on one side, laser drill through-holes, and no post-laser sintering by-products on the microfluidic pattern, the microfluidic channel pattern on the fluidic substrate extending along a surface of the fluidic substrate, away from the laser drill through-holes;
forming a sensing wafer having a plurality of bio-sensors;
depositing a photoresist on a sensing surface side of the sensing wafer;
exposing an exposure portion of the photoresist;
washing a removal portion of the photoresist off the sensing wafer, while leaving a remaining portion of the photoresist on the sensing wafer, to form a first pattern on the sensing surface;
chemically modifying the first pattern;
forming a polymer pattern on the sensing wafer or on a microfluidic channel pattern side of the fluidic substrate; and
bonding the sensing wafer and the fluidic substrate via the polymer pattern.

10. The method of claim 9, wherein the step of chemically modifying the first pattern comprises bio-functionalizing surfaces of the pattern.

11. The method of claim 10, further comprising:
depositing a second photoresist on a sensing surface side of the sensing wafer;
exposing an exposure portion of the second photoresist;
washing a removal portion of the second photoresist off the sensing wafer to form a second pattern on the sensing surface; and
bio-functionalizing the second pattern, wherein the first pattern and the second pattern are bio-functionalized differently.

12. The method of claim 9, wherein the step of chemically modifying the first pattern comprises rendering pattern hydrophobic or hydrophilic.

13. The method of claim 9, further comprising removing the remaining portion of the photoresist from the sensing wafer.

14. The method of claim 9, wherein the polymer is polysilesequioxane (PSQ).

15. The method of claim 9, wherein the polymer pattern is formed on the fluidic substrate by spin-on depositing of a photoresist, exposing the photoresist to the microfluidic channel pattern, removing the photoresist from the microfluidic channels, and baking a remaining portion of the photoresist.

16. The method of claim 15, wherein the bonding the sensing wafer and the fluidic substrate comprises treating a surface of the polymer on the fluidic substrate with plasma and alignably contacting the sensing wafer and the fluidic substrate, wherein a sensing wafer temperature does not exceed about 60 degrees Celsius during the bonding.

17. A method of manufacturing a biochip, comprising:
forming on a fluidic substrate a microfluidic channel pattern, the microfluidic channel pattern having laser drill through-holes;
removing post-laser sintering by-products on the microfluidic channel pattern;
forming a polymer pattern on a sensing wafer or on a microfluidic channel pattern side of the fluidic substrate, the sensing wafer having a pattern of modified surface; and
bonding the sensing wafer and the fluidic substrate via the polymer pattern after forming the microfluidic channel on the fluidic substrate, the bonding being done in a manner that the microfluidic channel pattern on the fluidic substrate extends away from the through-holes and along an interface of the fluidic substrate and the sensing wafer.

18. The method of claim 17, wherein the step of removing post-laser sintering by-products on the microfluidic channel pattern comprises;
depositing a sacrificial protective layer over the microfluidic channel pattern before forming the laser drill through-holes; and
removing the sacrificial protective layer after forming the laser drill through-holes.

19. The method of claim 17, wherein the step of providing a sensing wafer having a pattern of modified surface comprises:
depositing a photoresist on a sensing surface side of the sensing wafer;
exposing an exposure portion of the photoresist;
washing a removal portion of the photoresist off the sensing wafer, while leaving a remaining portion of the photoresist on the sensing wafer, to form a first pattern on the sensing surface; and
chemically modifying the first pattern.

20. The method of claim 17, wherein the step of bonding the sensing wafer and the fluidic substrate via the polymer comprises bonding at a temperature of less than about 100 degrees Celsius.

* * * * *